US006005148A

United States Patent [19]
Tanielyan et al.

[11] Patent Number: 6,005,148
[45] Date of Patent: Dec. 21, 1999

[54] SUPPORTED CATALYSTS

[75] Inventors: Setrak K. Tanielyan, Maplewood; Robert L. Augustine, Livingston, both of N.J.

[73] Assignee: Seton Hall University, South Orange, N.J.

[21] Appl. No.: 09/193,604

[22] Filed: Nov. 17, 1998

Related U.S. Application Data

[62] Division of application No. 08/994,025, Dec. 18, 1997
[60] Provisional application No. 60/034,338, Dec. 23, 1996.

[51] Int. Cl.$^6$ ................................................. C07C 45/50
[52] U.S. Cl. ...................... 568/454; 568/882; 562/485; 562/554; 560/210; 502/154
[58] Field of Search ...................... 502/154, 155, 502/164, 204, 312; 560/218, 1, 37, 100, 104; 562/484; 585/267, 277; 568/426, 429, 451, 454, 882

[56] References Cited

U.S. PATENT DOCUMENTS

| 4,448,892 | 5/1984 | Kukes et al. ............................ 502/164 |
| 4,590,298 | 5/1986 | Che ......................................... 568/387 |
| 4,612,301 | 9/1986 | Currie et al. ........................... 502/154 |

(List continued on next page.)

OTHER PUBLICATIONS

John C. Bailar, Jr., "Heterogenizing" Homogeneous Catalysts, Cat. Rev. –Sci. Eng., 10(1), 17–36 (1974).
Yusuke Izumi et al., "Catalysis of Heteropoly Acids Entrapped in Activated Carbon", Chemistry Letters, 663–666 (1981).
David C. Bailey et al., "Immobilized Transition–Metal Carbonyls and Related Catalysts", Chemical Reviews, 81(2), 109–148 (1981).
Yusuke Izumi et al., "Catalysis by Heterogeneous Supported Heteropoly Acid", Journal of Catalysis, 84, 402–409 (1983).
Hirosuki Wada et al., "Carbonylation of Olefins", Jpn. Kokai Tokkyo Koho JP 62,161,737, Chemical Abstracts, 131037 (1987).
Ronny Neumann et al., "A Ruthenium Heteropolyanion as Catalyst for Alkane and Alkene Oxidation", J. Chem. Soc. Chem. Commun., 1324–1325 (1989).
A.R. Siedle et al., "Solid–State Chemistry of Molecular Metal Oxide Clusters. Bis(triphenylphosphine)rhodium(I) Carbonyl Derivatives", Inorg. Chem., 29, 1667–1673 (1990).
Yusuke Izumi et al., "Heteropoly Anion–Modified Palladium Catalyst for Reductive Carbonylation of Nitrobenzene", Chemistry Letters, 795–796 (1990).
S. Kasztelan et al., "The Existence and Stability of the Silica–Supported12–Molybdophosphoric Acid Keggin Unit as Shown by Raman, XPS, and $^{31}$P NMR Spectroscopic Studies", Journal of Catalysis, 125, 45–53 (1990).
Yusuke Izumi, "Preparation of Aromatic Urethanes", Jpn. Kokai Tokkyo Koho JP 03 93,765, Chemical Abstracts, 115, 182846, 866–877 (1991).

Marco A. Schwegler et al., "Heteropolyacids as Catalysts for the Production of Phtalate Diesters," Applied Catalysis, 74, 191–204 (1991).
Taehyun Kwon et al., "Synthesis and Properties of Anionic Clays Pillared by $[XM_{12}O_{40}]^{n-}$ Keggin Ions", Journal of Molecular Catalysis, 74, 23–33 (1992).
A.M. Trzeciak et al., "Homogeneous and Alumina Supported Rhodium Complex Catalyzed Hydrogenation", Journal of Molecular Catalysis, 88, 13–22 (1994).
Matthias Pohl et al., "Polyoxoanion–Supported Catalyst Precursors. Synthesis and Characterization of the Iridium(I) and Rhodium(I) Precatalysts $[(n-C_4H_9)_4N]_5Na_3[1,5-COD) M•P_2W_{15}Nb_3O_{62}]$ (M=IR, Rh)", Inorg. Chem., 34, 1413–1429 (1995).
A.W. Stobbe et al, "Heteropolyanions as Redox Components in Heterogeneous Wacker Oxidation Catalysts", Journal of Catalysis , 154, 175–186 (1995).
Guo–Hua Liu et al., "Synthesis and Properties of Pillared Montmorillonite Formed by Intercalation of Transition Metal Macrocyclic Complexes", Microporous Materials, 5, 61–67 (1995).
Kam T. Wan et al., "Asymmetric Synthesis of Naproxen by a New Heterogeneous Catalyst", Journal of Catalysis, 152, 25–30 (1995).
Takafumi Shido et al., "$Rh_4$ Carbonyl Clusters Coordinated With Tris(Hydroxymethyl)phosphine Grafted Onto $SiO_2$ Surfaces and Structural Control of Active sites in Gas–Phase Olefin Hydroformylation Reactions", Journal of Catalysis, 157, 436–449 (1995).
Patrick Gamez et al., "Homogeneous and Heterogeneous Pd–catalyzed Enantioselective Alkylation With $C_2$–symmetric Chiral Nitrogen Ligands", Tetrahedron: Asymmetry, 6(5), 1109–1116 (1995).
Yusuke Izumi et al., "Silica–included Heteropoly Compounds as Solid Acid Catalysts", Microporous Materials, 5, 255–262 (1955).
Filippo Minutolo et al., "Polymer–Bound Chiral (Salen) Mn(III) Complex as Heterogeneous Catalyst in Rapid and Clean Enantioselective Epoxidation of Unfunctionalised Olefins", Tetrahedron Letters, 37 (19), 3375–3378 (1996).
Ulrich Nagel et al., "Synthesis of Bis (phosphane) Palladium and Rhodium Complexes on a Polyethylene Oxide Grafted Polystyrene Matrix (TentaGel) and the Catalytic Behavior of the Rhodium Complexes", Chem. Ber., 129, 815–821 (1996).
Vera Isaeva et al., "Synthesis of Ru, Rh and Pd Complexes Immobilized on Modified Supports. Investigation of the Hydrogenation of Cinnamaldehyde", Bull Soc Chim Fr, 133, 351–357 (1996).

*Primary Examiner*—Shailendra Kumar
*Assistant Examiner*—Sreeni Padmanabhan
*Attorney, Agent, or Firm*—Scully, Scott, Murphy & Presser

[57] ABSTRACT

A supported catalyst comprising a support, an anchoring agent such as a heteropoly acid or anion, and a metal complex which is useful in a wide variety on organic reactions, especially the hydrogenation of substituted α,β unsaturated acids and esters, is provided. Various methods of preparing the supported catalyst of the present invention is also disclosed.

29 Claims, 1 Drawing Sheet

U.S. PATENT DOCUMENTS

| | | | |
|---|---|---|---|
| 4,673,753 | 6/1987 | Siedle | 556/15 |
| 5,116,796 | 5/1992 | Edlund et al. | 502/154 |
| 5,225,598 | 7/1993 | Doumaux, Jr. et al. | 564/480 |
| 5,225,599 | 7/1993 | King et al. | 564/480 |
| 5,250,739 | 10/1993 | Mizuno et al. | 568/360 |
| 5,254,714 | 10/1993 | Ramezanian | 560/8 |
| 5,489,733 | 2/1996 | Soled | 585/740 |
| 5,580,991 | 12/1996 | Sugiyama et al. | 549/325 |

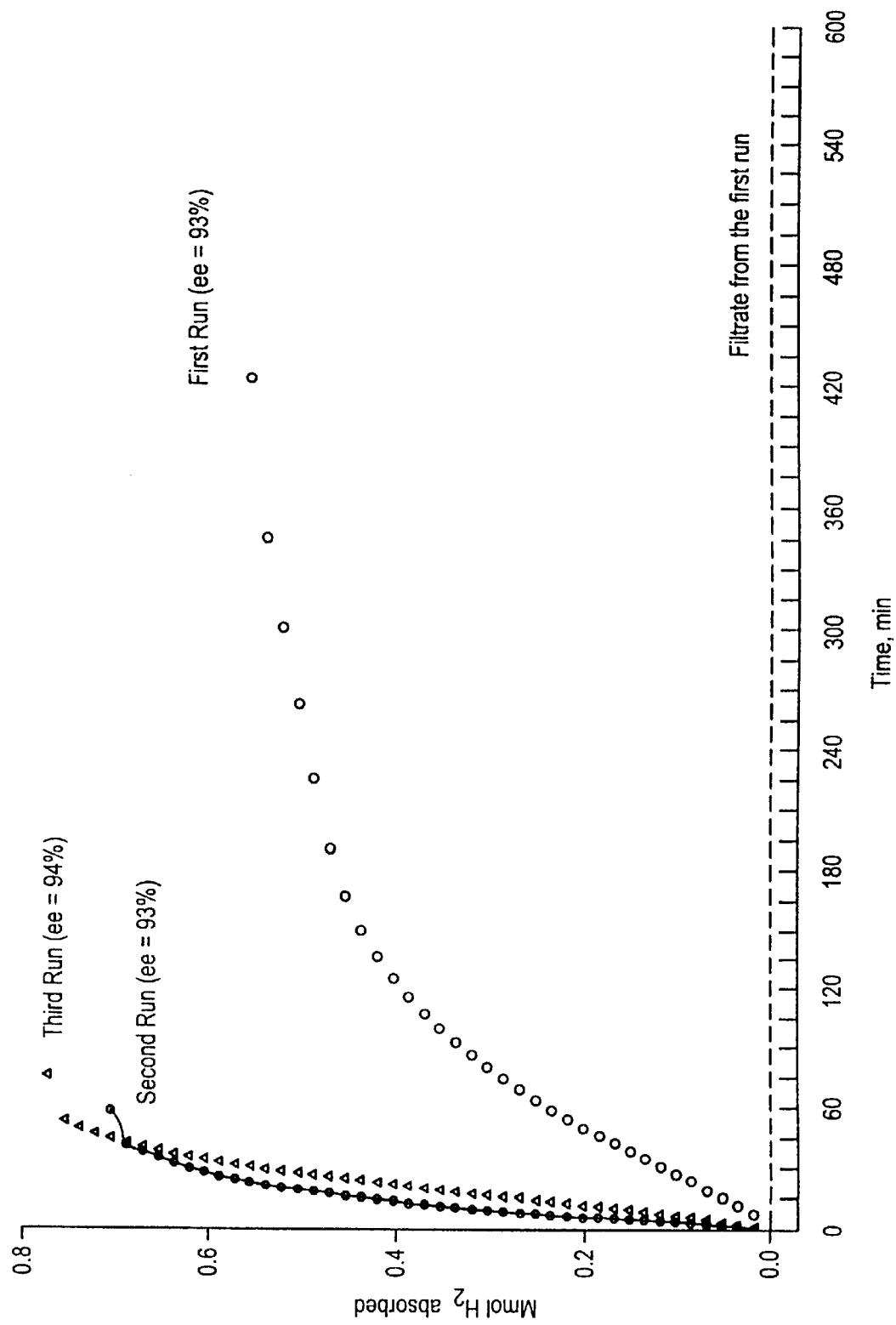

SUPPORTED CATALYSTS

RELATED APPLICATIONS

This application claims benefit of provisional application U.S. Ser. No. 60/034,338, filed Dec. 23, 1996. This application is a divisional of U.S. application Ser. No. 08/994, 025, filed Dec. 18, 1997.

This patent research project was supported in part by a grant from the National Science Foundation, Grant No. CTS-9312533.

FIELD OF THE INVENTION

The present invention relates to a highly stable supported catalyst which exhibits high reactivity and selectivity in a wide variety of organic reactions. More specifically, the present invention relates to a supported catalyst which comprises a support, an anchoring agent and a metal complex, wherein the anchoring agent is a heteropoly acid, its lacunar or other crystalline or noncrystalline phases or their anions. Such a supported catalyst is particularly useful for, but not limited to, the chiral hydrogenation of substituted α,β unsaturated acids or esters and α- or β-ketoesters or lactones. Various methods of preparing the supported catalyst of the present invention are also provided herein.

BACKGROUND OF THE INVENTION

Catalytic processes using either homogeneous catalysts, i.e. those present in the same phase as the reactant, or heterogeneous catalysts, i.e. those present as a separate phase in the reaction medium, have played an important role in organic synthesis. Heterogeneous catalysts are insoluble; thus they can be readily separated from the reaction mixture and, generally, offer the potential for ready re-use. Despite these advantages, prior art heterogeneous catalysts are rather limited in the number and types of organic reactions in which they can be used. In addition, they are usually less selective than homogeneous catalysts which are typically soluble metal salts or metal complexes. Indeed, homogeneous catalysts are not only more selective than heterogeneous catalysts, but have been used to promote a wider variety of organic reactions. Nevertheless, difficulties can be encountered in separating the soluble, homogeneous catalyst, both the metal and the accompanying ligands, from the product. This not only presents problems with the purity of the product, but also makes the re-use of the homogeneous catalyst problematic. The potential loss of the ligand is particularly serious in enantioselective reactions where chiral ligands are usually quite expensive.

Over the past twenty-five years, attempts have been made to "heterogenize" the more versatile homogeneous catalysts, the primary aim being to maintain reaction activity and selectivity of the homogeneous species while at the same time significantly increasing the ease of separation from the reaction medium. One such approach to achieve "heterogenization" involves reacting a metal complex or salt with a solid support such as a polymer or a metal oxide which had been previously modified by the addition of phosphine or amine ligands to the surface of the support. *Catalysis Reviews*, 16, 17–37 (1974) and *Chemical Reviews*, 81, 109 (1981) are reviews of the earlier literature concerned with polymer supported complexes. *Tetrahedron: Asymmetry*, 6, 1109–1116 (1995), *Tetrahedron Letters*, 37, 3375–3378 (1996) and *Chemische Berichte*, 129, 815–821 (1996) are examples of recent references in this area. From a practical approach, these catalysts are not widely used since their activities are frequently lower than those of the corresponding homogeneous analogs. In addition, problems associated with polymer swelling and attendant mass transport difficulties can be encountered, as well as the finding that activity is frequently lost on attempted re-use. Some success has been reported in preparing polymer supported chiral complexes, but the selectivity observed with the use of such "heterogenized" species has generally been lower than that obtained using the homogeneous catalyst itself.

"Catalysis by Supported Complexes", *Studies in Surface Science and Catalysis*, Volume 8, Elsevier Publishing Company, Amsterdam, 1981 is an extensive review of the earlier work concerned with the anchoring of metal complexes onto surface modified oxides. *Journal of Catalysis*, 157, 436–449 (1995) and *Bulletin Societe de Chemie*, France, 133, 351–357 (1996) are some more recent references. While these materials do not manifest significant swelling problems associated with the use of polymer supports, there are frequent reports of loss of activity on attempted re-use.

In rare instances, the oxide support does not have to be modified before the application of a metal complex. *Journal of Molecular Catalysis*, 88 13–22 (1994) describes the interaction of $Rh(OH)(CO)(PPh_3)_2$ with an alumina surface to give a supported catalyst for the hydrogenation of alkenes and benzene. This report also states that the presence of the Rh—OH entity is necessary for interaction with the surface of the alumina and that other complexes could not be attached to the oxide surface.

Another problem associated with prior art catalysts made from metal complexes which are attached to either a modified polymer or metal oxide surface is that their preparation techniques are rather specific and are driven by the nature of the ligand to be attached. Hence, modification of the catalyst to introduce another, more selective ligand is usually an arduous and complex task, if it is one that can be accomplished at all. This circumstance has particular importance where the preparation of enantioselective catalysts are concerned since optimal enantiomeric excess is usually obtained using a specific ligand or class of ligands for a given reaction or substrate.

*Journal of Catalysis*, 152, 25–30 (1995) describes the preparation of chiral, supported aqueous-phase catalysts and their use in the, preparation of naproxen. These heterogeneous catalysts have the same enantioselectivity as the homogeneous counterpart, but are 2 to 2.5 times less active.

Heteropoly acids have long been used as solid acid catalysts and have been supported on various solid supports for use in this way. For instance, *Chemistry Letters*, 663 (1981) and *Applied Catalysis* 74, 191–204 (1991) describe the use of heteropoly acids supported on carbon as solid acid catalysts, while *Journal of Catalysis*, 84, 402–409 (1983), *Journal of Catalysis*, 125, 45–53 (1990) and *Microporous Materials*, 5, 255–262 (1995) describe the use of silica as a support for heteropoly acids. *Journal of Molecular Catalysis*, 74, 23–33 (1992) describes the pillaring of anionic clays by heteropoly acids.

It has been known for some time that interaction of a heteropoly acid with a metal salt can provide catalysts that are useful for a number of different oxidation and related reactions in which the redox properties of the heteropoly acid play an important role. For instance, U.S. Pat. No. 4,448,892 and *Journal of Catalysis*, 154, 175–186 (1995) describe the use of such catalysts, where the same are prepared using a palladium salt, for the oxidation of alkenes to aldehydes or ketones. Similar catalysts have also been used for the carbonylation of alkenes as described in Jpn. Kokai Tokkyo Koho JP 62, 161,737 [Chemical Abstracts, 108, 131037 (1988)]. The carbonylation of nitro aromatics is described in *Chemistry Letters*, 795–796 (1990) and Jpn. Kokai Tokkyo Koho JP 03, 93,765 [Chemical Abstracts, 115, 182846 (1991)] while alkane and alkene oxidations are described in Chemical Communications, 1324–1325 (1989).

U.S. Pat. Nos. 5,116,796 and 5,250,739 as well as *Inorganic Chemistry*, 34, 1413–1429 (1995) describe the formation of soluble iridium-heteropoly acid complexes which have been used to promote alkene hydrogenations and oxidations.

U.S. Pat. No. 4,590,298 describes the use of soluble rhodium cyclopentadiene complexes in combination with heteropoly acids for the reaction of hydrogen and carbon monoxide with formaldehyde to give $C_4$–$C_5$ hydroxy ketones.

*Chemistry Letters*, 1595 (1985) describes the interaction of $RhCl(PPh_3)_3$ with $Li_4SiMo_{12}O_{40}$ to give a soluble catalyst for the semihydrogenation of methyl phenyl acetylene.

U.S. Pat. No. 4,673,753 and *Inorganic Chemistry*, 29, 1667–1673 (1990) describe the combination of rhodium carbonyl phosphine complexes with heteropoly acids. The substances prepared are insoluble in toluene so the catalytic reactions are run in this solvent to maintain a heterogeneous catalyst system. These species are used to catalyze the oxidation of CO by NO, the isomerization of 1-hexene and the hydroformylation of 1-hexene. There is no report on the re-use of these catalysts.

Despite the current state of the art, there is a continuing need to develop stable heterogeneous catalysts which employ an active metal complex on an insoluble support, which catalysts are highly reactive and selective in organic reactions. Indeed, a particular need exists for the development of such catalysts which contain a chiral metal entity capable of promoting an enantioselective reaction. The term "chiral metal entity" is used herein to denote metal complexes which contain at least one chiral ligand.

SUMMARY OF THE INVENTION

One aspect of the present invention relates to a supported catalyst which comprises the following catalyst components: (i) a particulate support; e.g. an inorganic oxide or carbon; (ii) an "anchoring agent"; and (iii) a metal complex. By "anchoring agent" is meant a heteropoly acid, its lacunar or other crystalline or non-crystalline phase material or their anions. By "metal complex" is meant any catalytically active material which contains at least one transition metal atom or ion from Group IIIB, IVB, VB, VIB, VIIB, VIII, IB or IIB of the Periodic Table of Elements to which one or more ligands are attached. The ligands can be species containing, for instance, phosphorous, nitrogen, oxygen, sulfur, halogen or atoms having an electron pair, as well as carbonyls, alkenes and dienes or other moieties which can coordinate with the transition metal atom or ion.

Another aspect of the present invention relates to a method of preparing the aforementioned supported catalyst. In accordance with this aspect of the present invention, the supported catalyst is prepared by the following steps:

(i) contacting a support with a heteropoly acid or anion under conditions effective to form a heteropoly acid or anion-containing support;

(ii) contacting a metal complex with said heteropoly acid or anion-containing support under conditions effective to form a supported catalyst;

(iii) activating the catalyst be either first use in the reactor or by a reduction step such as a prehydrogenation; and (iv) optionally, recovering said supported catalyst from.

In accordance with a second method of the present invention, the supported catalyst is obtained by the following steps:

(i) contacting a heteropoly acid or anion with a metal complex under conditions effective to form a solution or suspension containing said heteropoly acid or anion and said metal complex;

(ii) contacting a support with said solution or suspension prepared in step (i) under conditions effective to form a supported catalyst;

(iii) activating the catalyst be either first use in a reactor or by a reduction step such as a prehydrogenation; and (iv) optionally, recovering said supported catalyst from.

Another aspect of the present invention relates to a method of forming a supported catalyst which comprises the steps of:

(i) contacting a support with a heteropoly acid or anion under conditions effective to form a modified support comprising the heteropoly acid or anion;

(ii) contacting a catalytic precursor material with said support produced in step (i) under conditions effective to form a supported catalyst precursor;

(iii) contacting the supported catalyst precursor with a ligand under conditions effective to prepare a catalytically active supported catalyst;

(iv) activating the catalyst be either first use in a reactor or by a reduction step such as prehydrogenation; and (v) optionally, recovering said supported catalyst from.

In another aspect of the present invention, the supported catalyst can be used to promote a wide variety of organic reactions which include, but are not limited to: hydrogenations, dehydrogenations, isomerizations, carbonylations, hydrogenolyses, hydroformylations, oxidations, carboxylations, aminations, silylations, carboalkoxylations, cyclopropanations, alkylations, allylations, arylations and other carbon—carbon bond forming reactions. These reactions can be run in either the vapor phase or in solution. Further, they can be run in either a batch mode or in a continuous process.

Of particular importance is the use of the chiral supported catalyst of the present invention for the enantioselective hydrogenation of prochiral compounds such as substituted α,β unsaturated acids or esters and α- or β-ketoesters or lactones.

A related process involves the use of the supported catalyst of the present invention to promote the hydroformylation of alkenes into aldehydes and/or alcohols in the presence of CO and $H_2$ under conditions which are sufficient to convert said alkene into the corresponding aldehyde and/or alcohol.

BRIEF DESCRIPTION OF THE DRAWING

FIG. 1 is a plot of the hydrogen uptake curves for the hydrogenation of 2-acetamidocinnamic acid methyl ester using a Rh(Me-DUPHOS)(COD) catalyst supported on a phosphotungstic acid modified carbon support prepared in accordance with the present invention.

DETAILED DESCRIPTION OF THE INVENTION

As stated hereinabove, the present invention allows a homogeneous catalyst to be supported with high activity, selectivity and stability in a wide variety of organic reactions. Specifically, the catalyst of the present invention comprises the following three components: an insoluble support, an anchoring agent (a heteropoly acid, its lacunar or other crystalline or non-crystalline phases or their anions), and a metal complex. The supported catalyst of the present invention is stable in air while retaining or even surpassing the activity and selectivity of the corresponding homogeneous catalyst; but, being insoluble, it is easily removed from the reaction mixture and is thus capable of extended re-use. Moreover, the supported catalyst of the present invention quite unexpectedly exhibits an increase in reactivity and selectivity after re-use. Thus, the supported catalyst of the present invention is highly useful in a wide variety of applications including, but not limited to, pharmaceutical and agrochemical applications.

The support is a particulate amorphous or crystalline material having a sufficient surface area to facilitate uniform distribution of the anchoring agent thereon. A particle size is selected to afford easy separability from the reaction media, and may typically range from 100–200 mesh.

The supported catalyst of the present invention can be made using any of the following methods. In the first method, a support is contacted with a heteropoly acid or anion under conditions which are effective to form a support which contains the heteropoly acid or anion.

Suitable supports include, but are not limited to: metal oxides such as alumina, silica, titania, zirconia, lanthana, zeolites and clays, as well as carbon, resins, polymers and the like. The support may be used as is, or it may be treated prior to use to remove unwanted species which may adversely effect the activity of the catalyst. For example, the support may be calcined either in air or in an inert atmosphere prior to use.

The interaction between the anchoring agent and the support may be effected by reaction as discussed below; but it is to be understood that the anchoring agent may be bonded to or intercalated by the support solely by physical and/or chemical attractive forces based upon van der Waals forces, donor/acceptor interactions and other surface phenomena.

Another method of treating the support involves the use of a modifier which has been found to increase the adhesion of the heteropoly acid or anion to the support. Suitable modifiers that may be employed in the present invention for this purpose include, but are not limited to: metal alkoxides such as titanium alkoxide, aluminum alkoxide, silane alkoxide, vanadium alkoxide and the like; polyisocyanates, hydroxy epoxides, cyano epoxides and other functionalized organic materials. Of the aforementioned modifiers, metal alkoxides are particularly preferred.

When a modifier is employed in the present invention, the modifier is contacted with the support in a solvent at a temperature of from about −25° to about 250° C. for a period of time of from about 1 min. to about 50 hrs. The amount of modifier employed in the present invention varies depending upon the type of support being employed. Typically, however, the modifier is present in about 0.01% to about 100% by weight of the support employed in the present invention.

As stated above, the support, either treated or nontreated, is then contacted with a heteropoly acid or anion. The heteropoly acids employed in the present invention are conventional heteropoly acids well known to those skilled in the art. The term "heteropoly acid" is used herein to denote any polyprotic mixed oxide which is generally composed of a central ion or ions bonded to an appropriate number of oxygen atoms and surrounded by a near spherical shell of octahedral oxometal species joined together by shared oxygen atoms. The central atom or "heteroatom" is typically a cation having a $+3$ to $+5$ oxidation state such as $P^{+5}$, $As^{+5}$, $Si^{+4}$ or $Mn^{+4}$. The metal species associated with the octahedra are usually Mo, W or V. The octahedra in the shell of the heteropoly acid can be of uniform composition or contain different metal species.

As discussed in "Zeolites, Clays and Heteropoly Acids in Organic Synthesis", Chapter 3, VCH Publishers, New York, 1992, suitable heteropoly acids include, but are not limited to: Keggin species such as phosphotungstic acid (PTA), phosphomolybdic acid (PMA), silicotungstic acid (STA) and the like; Dawson species; Waugh species; Anderson species; Silverton species; their lacunar and other crystalline or non-crystalline forms; and anions of the preceding. When anions are used, the counterions can be, but are not limited to: alkali, alkali earth or quaternary ammonium ions.

Contact of the support and the heteropoly acid or anion generally occurs in a solvent at a temperature of from about −25° to about 250° C. for a time period of from about 1 min. to about 50 hrs. Preferably, this occurs at temperatures of between about 25° and about 75° C. for periods of between 3 and 12 hours. Typically, in the present invention the heteropoly acid or its anion is present in a weight ratio with the support of from about 0.01:1 to about 20:1. This contact step may occur in air or it may be carried out in an inert atmosphere.

In accordance with the next step of the present invention, the heteropoly acid or anion-containing support is contacted with a metal complex under conditions which are effective to form a supported catalyst. By "metal complex" is meant any catalytically active material which contains at least one transition metal atom or ion from Group IIIB, IVB, VB, VIB, VIIB, VIII, IB or IIB of the Periodic Table of Elements to which one or more ligands are attached. Suitable transition metal atoms or ions include: Sc, Y, Ti, Zr, Hf, V, Cr, Mo, W, Mn, Re, Fe, Ru, Os, Co, Rh, Ir, Ni, Pd, Pt, Cu, Ag, Au, Zn and the like. Preferably, the metal complex will contain a metal atom or ion from Group VIII of the Periodic Table of Elements; e.g., Fe, Ru, Os, Co, Rh, Ir, Ni, Pd and Pt.

The ligands can be species containing, for instance, phosphorus, nitrogen, oxygen, sulfur, halogen or atoms having a free electron pair, as well as carbonyls, alkenes and dienes or other moieties which can coordinate with the metal atom or ion. Suitable achiral ligands which may be employed in the present invention include, but are not limited to: species such as cyclopentadiene, carbon monoxide, cyclooctadiene (COD) and tertiary phosphines. Suitable chiral ligands which may be employed in the present invention include, but are not limited to: species such as (R,R) or (S,S) 2,2'-bis(diphenylphosphino)1,1'-binaphthyl (BINAP), (2S,3S)-bis(diphenylphosphino) butane (CHIRAPHOS), 2,3-O-isopropylidene-2,3-dihydroxy-1,4-bis(diphenylphosphino)butane (DIOP), (R,R)-1,2-bis[(2-methoxyphenyl)phenylphosphino]ethane (DIPAMP), 1,2-bis(2R,5R)-2,5-(dimethylphospholano) benzene (Me-DUPHOS) and (R) 1,2-bis (diphenylphosphino)propane (PROPHOS). Mixtures of these ligands such as (COD) (Me-DUPHOS) are also contemplated herein. The use of chiral ligands is particularly preferred in the present invention for promoting enantioselective reactions.

Examples of metal complexes contemplated by the present invention include, but are not limited to: Rh(COD)

(DIPAMP)BF$_4$, Pd(R,R-BINAP)Cl$_2$, Rh(COD) (Me-DUPHOS)Cl and the like. In addition to metal complexes, other catalytically active compounds containing a Group VIII metal are also contemplated herein. Examples of such catalytically active compounds include, but are not limited to: the elemental Group VIII metals, Group VIII metal salts, and the like.

The contacting step between the heteropoly acid or anion-containing support and the metal complex typically occurs in a solvent and at a temperature of from about −25° to about 250° C. for a time period of from about 1 min. to about 50 hrs. Preferably this contacting takes place at temperatures of between about 25° and about 50° C. for a time period of between about 1 hr and about 3 hrs. Generally in the present invention, the metal complex is employed at a concentration such that the metal complex to heteropoly acid or anion molar ratio is from about 0.1:1 to about 6:1; more preferably, from about 0.5:1 to about 1.5:1; and most preferably from about 0.75:1 to about 1:1.

The solvents employed in various steps of the present invention may be the same or different, and are those which are capable of dissolving the anchoring agent and/or the metal complexes. A preferred solvent is methanol, but other alcohols such as ethanol, propanol, hexanol, heptanol and the like, as well as water, ethers, esters, ketones and aliphatic or aromatic hydrocarbons, may also be employed in the present invention. The solvent may be employed as is, or it may be purified by techniques well known in the art prior to its use. For example, the solvent can be distilled and then passed over a bed or column containing an appropriate adsorbent material.

The solid supported catalyst of the present invention may then be activated either by first use in a reactor or by a reduction step such as a prehydrogenation.

The solid supported catalyst of the present invention may then be optionally recovered using techniques well known to those skilled in the art. For example, the solid catalyst may be recovered by decantation, filtration or centrifugation. The recovered solid catalyst may be used as is; or it may be washed with one of the aforementioned solvents prior to use to remove any anchoring agent or metal complex that is not bound to the support. The supported catalyst can then be dried.

In accordance with the second method of preparing the supported catalyst of the present invention, the anchoring agent mentioned hereinabove is contacted first with a metal complex to form a solution or suspension and then that solution or suspension is contacted with a support.

The contact between the anchoring agent and the metal complex typically occurs in a solvent at a temperature of from about −25° to about 250° C. for a period of time of from about 1 min. to about 50 hrs. Preferably, this contact takes place at temperatures of between about 25° to about 60° C. for periods of time from about 15 min to about 1 hr. Generally the metal complex is employed at a concentration such that the metal complex to anchoring agent molar ratio is from about 0.1:1 to about 6:1; more preferably, from about 0.5:1 to about 1.5:1; and most preferably from about 0.75:1 to about 1:1.

The resulting solution or suspension containing the anchoring agent and the metal complex may be used as is, or, in another embodiment of the present invention, the resulting solution or suspension is dried and then slurried in a comparable solvent prior to contacting with the metal complex. The solvents employed in this embodiment of the present invention are the same as those previously mentioned hereinabove.

The solution or suspension containing the anchoring agent and metal complex is then contacted with one of the supports mentioned above. This contact between the solution or suspension and the support generally occurs in a solvent at a temperature of from about −25° to about 250° C. for a period of time from about 1 min. to about 50 hrs. Preferably, this contacting takes place at a temperature of about 25° C. to about 60° C. for a period of time from about 3 hrs to about 12 hrs. In accordance with this aspect of the present invention, the anchoring agent and metal complex solution or suspension is present in about 0.01% to about 150% by weight of the support employed in this contacting step. The thus formed supported catalyst is, optionally, recovered as previously described.

The activation by prehydrogenation can be accomplished by stirring the supported catalyst under hydrogen typically at temperatures between ambient and 50° C. and at pressures between 1 and 10 atm. for an appropriate amount of time to achieve activation.

In accordance with another aspect of the present invention, a supported catalyst is prepared by first contacting a support with an anchoring agent as described hereinabove. The support containing the anchoring agent is then contacted with a catalyst precursor material under conditions which are effective for forming a supported catalyst precursor.

By "catalyst precursor material" is meant any metal salt or complex which is used to prepare a catalytically active entity. Examples of suitable catalyst precursors include, but are not limited to, rhodium cyclooctadiene dimer, ruthenium cyclooctadiene dimer, allyl palladium dimer, rhodium chloride and the like.

The contacting of the anchoring agent-containing support and the catalyst precursor typically occurs in a solvent at a temperature of from about −25° to about 250° C. for a time period of from about 1 min. to about 50 hrs. Preferably this contacting takes place at temperatures of between about 25° and about 50° C. for periods of between about 1 hr to about 3 hrs. Generally in the present invention, the catalyst precursor material is employed at a concentration such that the precursor to anchoring agent molar ratio is from about 0.1:1 to about 6:1; more preferably, from about 0.5:1 to about 1.5:1; and most preferably from about 0.75:1 to about 1:1. The catalyst supported precursor, optionally, may be washed and dried prior to treatment with a ligand.

The thus formed catalyst supported precursor is then contacted with a ligand which forms a catalytically active entity. It is noted that the catalyst supported precursor itself may or may not be catalytically active. It is, however, converted to a catalytically active entity by contacting it with a suitable ligand. The ligands employed for this purpose include those ligands mentioned hereinabove.

The concentration of the ligand which is added to the catalyst supported precursor is typically from about 1 to about 6 mmol per mmol of catalyst precursor material. The treatment of the catalyst supported precursor and the ligand typically occurs in a solvent at temperatures of from about −25° to about 250° C. for periods of from about 1 min to about 50 hrs.

It should be mentioned that all of the above contacting steps may be conducted in air or they may be done in hydrogen or in an inert gas atmosphere, as appropriate. The activation by prehydrogenation is carried out using the conditions mentioned hereinabove.

The above description illustrates the methods which can be used in forming the supported catalyst of the present invention. It is emphasized that all three catalyst components of the present invention, i.e. the support, the anchoring agent, and the metal complex are needed for optimum catalytic activity, stability and selectivity. Catalysts not containing all three catalyst components of the present invention exhibit inferior results. For example, while catalysts prepared without the presence of the anchoring agent may sometimes show activity, the stability and activity in all cases is significantly lower than that of the supported catalyst of the present invention. In an appropriate solvent the heteropoly acid-metal complex product without the support may appear to be insoluble. While this material may be used as a heterogeneous catalyst a portion of the catalytically active species does dissolve resulting in a loss of catalyst.

The supported catalyst of the present invention imparts improved catalytic properties such as catalytic activity, stability and selectivity as compared to the corresponding homogeneous catalyst or as to catalytic species prepared only from a heteropoly acid and a metal complex. Moreover, the supported catalyst of the present invention advantageously and unexpectedly exhibits an increase in catalytic activity and selectivity when the catalyst is re-used. Without wishing to be bound by any theory it is thought that the observed increase in activity and selectivity when compared to the soluble species is the result of changes in the steric environment of the active metal in the supported moiety. Increases in stability may be brought about by the presence of the anchoring agent.

The catalyst itself comprises a relatively uniform distribution of active catalytic sites formed about the supporting particles, but remote therefrom to the extent of the selected anchoring agent bridge. This shell of active sites may typically be present at a distance, for example, 10–14 Å from the support particle itself, thereby affording excellent accessibility to reactants.

A further advantage of the supported catalyst of the present invention is that it is insoluble; and leaching of the metal, which is common with prior art supported homogeneous catalysts, is not observed.

In view of the above advantages, the supported catalyst of the present invention can be used to promote a wide variety of organic reactions which include, but are not limited to: hydrogenations, dehydrogenations, isomerizations, carbonylations, hydrogenolyses, hydroformylations, oxidations, carboxylations, aminations, silylations, carboalkoxylations, cyclopropanations, alkylations, allylations, arylations and other carbon—carbon bond forming reactions. These reactions can be run in either the vapor phase or in solution. Further, they can be run in either a batch mode or in a continuous process using conditions well known to those skilled in the art.

In a highly preferred embodiment of the present invention, the supported catalyst of the present invention is employed in hydrogenating substituted $\alpha,\beta$ unsaturated acids or esters or other prochiral substrates. In accordance with this aspect of the present invention, a substituted $\alpha,\beta$ unsaturated acid or ester having the formula

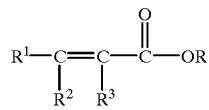

wherein $R^1$, $R^2$ and $R^3$ are the same or different and are hydrogen, alkyl containing from 1 to about 35 carbon atoms, alkenyl containing from 1 to about 35 carbon atoms, alkynyl containing from 1 to about 35 carbon atoms, aryl containing from about 6 to about 18 carbon atoms, amine, amide, or alkoxide containing from about 1 to about 35 carbon atoms, and R is hydrogen or alkyl having from about 1 to about 35 carbon atoms, is contacted with a supported catalyst of the present invention in the presence of $H_2$ under conditions which are effective to selectively hydrogenate the substituted $\alpha,\beta$ unsaturated acid or ester into a desired product. It is noted that the above substituents may be straight or branched as well as being unsubstituted or substituted with one of the substituents mentioned hereinabove. The aryl substituents may also be bicyclic or fused species.

Of particular interest is the enantioselective hydrogenation of those compounds in which $R^3$ is not hydrogen or $R^1$ is different from $R^2$ and neither is hydrogen. Hydrogenation of these prochiral substrates over a chiral supported catalyst of the present invention leads to the selective formation of one of the enantiomers of the product.

Preferred substituted $\alpha,\beta$ unsaturated acids or esters contemplated by the present invention include, but are not limited to: 2-acetamidocinnamic acid methyl ester, 2-acetamidocinnamic acid, 2-acetamidoacrylic acid methyl ester, 2-acetamidoacrylic acid, dimethylitaconate, itaconic acid, 2-methylpentenoic acid, 2-methylhexenoic acid, and 2-(6-methoxy-2-naphthyl)acrylic acid.

In another preferred embodiment of the present invention, the supported catalyst of the present invention is employed in hydrogenating carbonyl groups, particularly prochiral ketones, $\alpha$-ketoesters, $\alpha$-ketolactones or $\beta$-ketoesters.

The hydrogenation conditions employed in the present invention are those that are typically employed in the prior art for carrying out such a reaction.

In yet another preferred embodiment of the present invention, a process for hydroformylating alkenes into their corresponding aldehydes and/or alcohols is provided. In accordance with this aspect of the present invention, an alkene containing from 2 to about 35 carbon atoms is contacted with a supported catalyst of the present invention in the presence of $H_2$ and CO and under conditions effective to convert the alkene to the desired product. The hydroformylation reaction may be carried out in the gas phase or in the liquid phase using conditions well known to those skilled in the art.

The following examples are given to illustrate the scope of the present invention. Because these examples are given for illustrative purposes only, the invention embodied herein should not be limited thereto.

EXAMPLE I

This example illustrates a procedure for the preparation of a supported catalyst prepared in accordance with the method of the present invention described above.

Four grams of the support material was suspended in 30 mL of methanol and stirred for 15 minutes after which time a solution of 200 micromoles of the heteropoly acid in 25 mL of methanol was added over a short time. The resulting mixture was stirred at room temperature for 60 minutes. A solution of 200 micromoles of the metal complex catalyst in 10 mL of methanol was then added slowly under vigorous stirring. After the addition was completed, stirring at room temperature was continued for about eight to about twelve hours after which time the suspension was transferred to a centrifuge tube and the solid separated by centrifugation. After decantation of the supernatant liquid, the solid was washed several times with methanol until no color was observed in the wash liquid. The residue was dried under vacuum and stored in a screw capped vial until use.

EXAMPLE II

This example illustrates a second procedure for the preparation of a supported catalyst prepared in accordance with the method of the present invention described above.

To a catalytic reactor was added 10 mL of methanol and 100 mg of the support material. After stirring for 15 minutes in air, a solution of 20 micromoles of the heteropoly acid in 2.5 mL of methanol was added and the suspension stirred for 30 minutes at room temperature. To this mixture was slowly added 1 mL of methanol containing 20 micromoles of the metal complex catalyst and the suspension stirred at room temperature for several hours in air and the stirring stopped. After the catalyst had settled, the liquid was withdrawn with a syringe and a 15 mL portion of methanol was added to the reactor. The mixture was stirred again for about 30–45 minutes, and the liquid again withdrawn. This washing procedure was repeated at least three times or until no color was observed in the wash liquid. After this, the air in the reactor was replaced with hydrogen, a solution of the reaction substrate was introduced into the reactor and the reaction initiated.

EXAMPLE III

This example illustrates a third procedure for the preparation of a supported catalyst in accordance with the method of the present invention.

To a catalytic reactor was added 10 mL of methanol and 300 mg of the support material. The reactor was filled with an inert gas and sealed with all further additions made through a septum adapter. After stirring for 15 minutes, a solution of 20 micromoles of the heteropoly acid in 2.5 mL of methanol was added and the suspension stirred for 30 minutes at room temperature. To this mixture was slowly added 1 mL of methanol containing 20 micromoles of the metal complex catalyst and the suspension stirred for several hours at room temperature and the stirring stopped. After the catalyst had settled, the liquid was withdrawn with a syringe and a 15 mL portion of methanol was added to the reactor. The mixture was stirred again for about 30 to 45 minutes, and the liquid again withdrawn. This washing procedure was repeated at least three times or until no color was observed in the wash liquid. After this, the inert gas in the reactor was replaced with hydrogen, a solution of the reaction substrate was introduced into the reactor and the hydrogenation initiated.

EXAMPLE IV

This example illustrates a fourth procedure for the preparation of a supported catalyst of the present invention.

To a suspension of 1 gram of Norit carbon in 10 mL of methanol was added a solution of 200 micromoles of the heteropoly acid in 25 mL of methanol at a rate of 1 mL/min. After this addition was complete, a solution of 400 micromoles of a base such as NaOH in 15 mL of methanol was added at the same rate and the resulting suspension was stirred at room temperature for an additional 12 hours. The suspension was centrifuged and the supernatant decanted. The modified support was washed with 20 mL portions of methanol until all of the soluble material had been removed. The solid was then dried under vacuum and stored in a glass vial until use. To a 180 mg portion of the modified support suspended in 3 mL of methyl acetate was added, with stirring, a solution of 25 micromoles of Pd(R,R-BINAP)Cl$_2$ in 3 mL of methylene chloride. The mixture was stirred at room temperature for about 12 hours, washed five times with 5 mL portions of methyl acetate and then used for an appropriate reaction. The supported catalyst can also be dried and stored for future use.

EXAMPLE V

This example describes the general procedure used for the hydrogenation of the various substrates over the catalysts prepared as described in the previous examples.

To a 25 mL reaction flask was added an amount of catalyst prepared by one of the procedures described in Examples I–III and containing 20 micromoles of the active metal complex. A solution of 0.82 millimoles of the reaction substrate in 10 mL of solvent was then added and the flask was evacuated and filled with hydrogen three times. The temperature and pressure in this reactor were set to the appropriate values and the reactor was stirred at such a rate as to avoid mass transfer control of the reaction to initiate the reaction. The amount of hydrogen taken up was measured by a computerized system for introducing into the reactor pulses containing known quantities of hydrogen. These pulses were introduced is into the reactor at such a rate as to maintain essentially a constant pressure of hydrogen in the reactor system with the time of each pulse also recorded by the computer. After hydrogen absorption ceased the catalyst was separated from the reaction solution and the product was analyzed by gas chromatography or HPLC using an appropriate column.

The results of some of these hydrogenations run using catalysts prepared using the procedures described in Examples I, II and III are listed in Tables 1 through 4.

EXAMPLE VI

This example illustrates the hydrogenation of 2-acetamidoacrylic acid methyl ester over a Rh(DIPAMP)/PTA/Montmorillonite Clay catalyst prepared using the procedure described in Example I where Moritmorillonite clay was used as the support material, phosphotungstic acid (PTA) was the heteropoly acid and Rh(COD) (DIPAMP)BF$_4$ was the metal complex catalyst.

A 25 mL reaction flask was placed 400 mg of the catalyst, Rh(DIPAMP)/PTA/Montmorillonite clay, prepared following the procedure described in Example I where Montmorillonite clay was used as the support material, phosphotungstic acid (PTA) was the heteropoly acid and Rh(COD) (DIPAMP)BF$_4$ was the metal complex catalyst. A solution of 1.26 millimoles of 2-acetamidoacrylic acid methyl ester in 10 mL of methanol was then added and the flask was evacuated and filled with hydrogen three times and the reaction initiated at atmospheric pressure and room temperature with computer monitoring of the hydrogen uptake. After hydrogen absorption ceased the product was analyzed by gas chromatography using a β-cyclodextrin Chiraldex column. As listed in Table 1 the hydrogen uptake occurred at a rate of 0.11 moles H$_2$/mole Rh/min with the product having an enantiomeric excess (ee) of 92%. After multiple re-use the catalyst had an activity of 0.80 moles H$_2$/mole Rh/min and the product had an ee of 92%. The activity and selectivity of this catalyst was retained after storage for at least eight months at room temperature in a screw capped vial in air as illustrated by the data given in Table 1.

EXAMPLE VII

This example illustrates the hydrogenation of 2-acetamidoacrylic acid methyl ester over a Rh(DIPAMP)/PTA/Montmorillonite clay catalyst prepared using the procedure described in Example III where Montmorillonite clay was used as the support material, phosphotungstic acid (PTA) was the heteropoly acid and Rh(COD) (DIPAMP)BF$_4$ was the metal complex catalyst.

A 25 mL reaction flask contained the catalyst prepared in a He atmosphere from 400 mg of Montmorillonite K, 20 micromoles of phosphotungstic acid (PTA) and 20 micromoles of the Rh(COD) (DIPAMP)BF$_4$ complex following the procedure described in Example III. A solution of 1.26 millimoles of 2-acetamidoacrylic acid methyl ester in 10 mL of methanol was then added and the flask was evacuated and filled with hydrogen three times and the reaction initiated at atmospheric pressure and room temperature with computer monitoring of the hydrogen uptake. After hydrogen absorption ceased, the product was analyzed by gas chromatography using a β-cyclodextrin Chiraldex column. As listed in Table 2, the hydrogen uptake occurred at a rate of 0.18 moles H$_2$/mole Rh/min with the product having an enantiomeric excess (ee) of 76%. After multiple re-use the catalyst had an activity of 0.56 moles H$_2$/mole Rh/min and the product had an ee of 91%.

EXAMPLE VIII

This example illustrates the hydrogenation of methyl 2-acetamidoacrylic acid methyl ester over a Rh(DIPAMP)/PTA/Al$_2$O$_3$ catalyst prepared using the procedure described in Example III where gamma alumina was used as the support material, phosphotungstic acid (PTA) was the heteropoly acid and Rh(COD)(DIPAMP)BF$_4$ was the metal complex catalyst.

A 25 mL reaction flask contained the catalyst prepared in a He atmosphere from 300 mg of gamma alumina, 20 micromoles of phosphotungstic acid (PTA) and 20 micromoles of the Rh(COD) (DIPAMP)BF$_4$ complex following the procedure described in Example III. A solution of 1.26 millimoles of 2-acetamidoacrylic acid methyl ester in 10 mL of methanol was then added and the flask was evacuated and filled with hydrogen three times and the reaction initiated at atmospheric pressure and room temperature with computer monitoring of the hydrogen uptake. After hydrogen absorption ceased the product was analyzed by gas chromatography using a β-cyclodextrin Chiraldex column. As listed in Table 2, the hydrogen uptake occurred at a rate of 0.32 moles H$_2$/mole Rh/min with the product having an enantiomeric excess (ee) of 90%. After multiple re-use the catalyst had an activity of 1.67 moles H$_2$/mole Rh/min and the product had an ee of 92%.

EXAMPLE IX

In this example, a Rh(COD) (DIPAMP)BF$_4$ catalyst was supported on various supports which were previously treated with phosphotungstic acid and the supported catalysts were used in the hydrogenation of 2-acetamidoacrylic acid methyl ester. The supported catalysts of this example were prepared using the procedure described in Example III using Montmorillonite K clay, carbon, aluminum and lanthana as the support materials.

The results of this experiment are shown in Table 2. Specifically, the data in Table 2 illustrate that the supported catalysts of the present invention exhibited high activity and selectivity after one use. Moreover, an unexpected increase in activity and selectivity was observed after the first use.

EXAMPLE X

In this example, a supported catalyst of the present invention was prepared using the procedure described in Example III using different heteropoly acids, i.e. phosphotungstic, silicotungstic and silicomolybdic. The support in each instance was Montmorillonite K clay and the metal complex was Rh(COD) (DIPAMP)BF$_4$. The supported catalysts prepared in this example were used in the hydrogenation of 2-acetamidoacrylic acid methyl ester.

The results of using different heteropoly acids in the preparation of the supported catalysts of the present invention are shown in Table 3. Again, the supported catalysts of this example showed good activity and selectivity after one use. An increase in activity and selectivity was unexpectedly observed after the first use.

EXAMPLE XI

In this example, a comparison between various homogeneous catalysts, namely Rh(DIPAMP), Rh(PROPHOS) and Rh(Me-DUPHOS), and the corresponding supported catalysts prepared in accordance with the present invention were made for the hydrogenation of 2-acetamidoacrylic acid methyl ester. The supported catalysts were prepared using the procedure described in Example III using gamma alumina as the support material and phosphotungstic acid (PTA) as the heteropoly acid and Rh(COD) (DIPAMP)BF$_4$, Rh(COD) (Me-DUPHOS)Cl and Rh(COD)(Me-DUPHOS) Cl, respectively, as the metal complex catalysts. The results of this study are shown in Table 4. Specifically, the data in Table 4 illustrate that the supported catalysts of the present invention exhibit efficient activity and selectivity when compared to their soluble homogeneous counterparts.

Moreover, the supported catalysts of the present invention unexpectedly exhibited an increase in activity and selectivity during re-use.

EXAMPLE XII

This example illustrates the hydrogenation of 2-acetamidocinnamic acid methyl ester over a Rh(Me-DUPHOS)/PTA/Carbon catalyst prepared using the procedure described in Example III where carbon was used as the support material, phosphotungstic acid (PTA) was the heteropoly acid and Rh(COD)(Me-DUPHOS)Cl was the metal complex catalyst.

A 25 mL reaction flask contained the catalyst prepared in a He atmosphere from 100 mg of carbon, 20 micromoles of phosphotungstic acid (PTA), 40 micromoles of NaOH and 20 micromoles of the Rh(COD)(Me-DUPHOS)Cl complex following the procedure described in Example III. A solution of 0.82 millimoles of 2-acetamidocinnamic acid methyl ester in 10 mL of methanol was then added and the flask was evacuated and filled with hydrogen three times and the reaction initiated at atmospheric pressure and room temperature with computer monitoring of the hydrogen uptake. After hydrogen absorption ceased the product was analyzed by gas chromatography using a β-cyclodextrin Chiraldex column. The hydrogen uptake occurred at a rate of 0.18 moles H$_2$/mole Rh/min with the product having an enantiomeric excess (ee) of 93%. After multiple re-use the catalyst had an activity of 0.97 moles H$_2$/mole Rh/min and the product had an ee of 94%.

EXAMPLE XIII

In this example, a Rh(Me-DUPHOS)(COD) BF$_4$ catalyst supported on a phosphotungstic acid modified carbon support prepared in accordance with Example III was used in the hydrogenation of 2-acetamidocinnamic acid methyl ester. The hydrogenation reactions were run at atmospheric pressure and at 25° C. The catalyst was re-used and the filtrate after the first hydrogenation showed no activity showing that there was no soluble catalyst present in the liquid.

The results of this experiment are shown in FIG. 1. Specifically, the activity of the catalyst increased after the first use.

EXAMPLE XIV

This example illustrates the hydrogenation of dimethylitaconate over a Ru(S,S-BINAP)/PTA/SuperFlow clay catalyst prepared using the procedure described in Example III where SuperFlow clay was used as the support material, phosphotungstic acid (PTA) was the heteropoly acid and Ru(SS-BINAP) (NEt$_3$)Cl$_2$ was the metal complex catalyst.

A 25 mL reaction flask contained the catalyst prepared in a He atmosphere from 200 mg of Clarion 470 SuperFlow clay, 10 micromoles of phosphotungstic acid (PTA) and 10 micromoles of the Ru(SS-BINAP)(NEt$_3$)Cl$_2$ complex following the procedure described in Example III. A solution of 1.42 millimoles of dimethylitaconate in 8 mL of methanol was then added and the flask was evacuated and filled with hydrogen three times and the reaction initiated at atmospheric pressure and room temperature with computer monitoring of the hydrogen uptake. After hydrogen absorption ceased the product was analyzed by gas chromatography using a β-cyclodextrin Chiraldex column. The hydrogen uptake occurred at a rate of 0.06 moles H$_2$/mole Ru/min with the product having an enantiomeric excess (ee) of 81%. After multiple reuse the catalyst had an activity of 0.09 moles H$_2$/mole Ru/min and the product had an ee of 91%.

EXAMPLE XV

This example illustrates the hydroformylation of 1-hexene over a Rh(P(C$_6$H$_5$)$_3$)$_3$Cl/PTA/Montmorillonite clay catalyst prepared using the procedure described in Example III where montmorillonite clay was used as the support material, phosphotungstic acid (PTA) was the heteropoly acid and Rh(P(C$_6$H$_5$)$_3$)$_3$Cl was the metal complex catalyst.

The modified support was prepared from a suspension of 1.5 g of Montmorillonite K in 10 mL of methanol and 120 micromoles of PTA in 5 mL of methanol. The catalyst was prepared from this support and 5 mL of toluene containing 100 micromoles of Rh(P(C$_6$H$_5$)$_3$)$_3$Cl. The resulting suspension was stirred at 70° C. overnight and the catalyst washed with 20 mL portions of toluene at least three times or until all of the soluble rhodium complex had been removed using the procedure described in Example III. To a 200 mg portion of this catalyst in a stainless steel autoclave was added 30 mL of toluene and 6 mL of 1-heptene. The autoclave was flushed three times with a 1:1 mixture of CO and H$_2$, pressurized to 1000 psig, the temperature was raised to 80° C. and stirring initiated at 800 rpm. The reaction was run for 24 hours after which time the liquid was removed and a second portion of 1-heptene and toluene were injected into the autoclave and the hydroformylation run again. This procedure was repeated three times with the products analyzed by GC-MS using a 30 m×0.25 mm HP-1 capillary column. The reaction data is listed in Table 5 along with corresponding data for the reaction run using a soluble Rh(P(C$_6$H$_5$)$_3$)$_3$Cl catalyst.

The isomerization product was 2-heptene (1) and the hydroformylation products were 1-octanal (2), 2-formylheptane (3) and 3-formylheptane (4). The foregoing numbers are utilized to identify the specific products in Table 5.

EXAMPLE XVI

This example illustrates the allylation of sodium dimethylmalonate by 2-butenyl acetate over a Pd(R,R-BINAP)/PTA/Carbon catalyst prepared using the procedure described in Example IV.

To the catalyst described in Example IV was added a solution of 160 mg of sodium dimethylmalonate in 5 mL of tetrahydrofuran and the suspension stirred for 10 minutes. 2-Butenyl acetate (60 microliters) was then added by syringe and the reaction mixture stirred at room temperature for 12 hours. The reaction liquid was then removed and analyzed by gas chromatography. The reaction data are listed in Table 6 along with data obtained on running the reaction using a soluble Pd(R,R-BINAP)Cl$_2$ catalyst.

The products were trans methyl (2-carbomethoxy)-4-hexenoate (5), cis methyl (2-carbomethoxy)-4-hexenoate (6) and (R) and (S) methyl (2-carbomethoxy-3-methyl)-4-pentenoate (7). The foregoing numbers are utilized to identify the specific products in Table 6.

EXAMPLE XVII

The example illustrates the preparation of a titanium alkoxide modified silica and its use as a support for Rh(P(C$_6$H$_5$)$_3$)$_3$Cl/PTA.

To a flask containing 100 mL of dry toluene was added 30 g of ICN60 silica which had been previously dried by heating at 90° C. for one hour under a vacuum of 18 mm Hg immediately before use. To this suspension was added in one portion a solution of 7.65 g of titanium isopropoxide in 30 mL of dry toluene and the flask was purged with nitrogen. The temperature of the suspension was slowly raised to 95°–100° C. and kept, with stirring, at that temperature overnight. After cooling, the solid was washed three times with 100 mL portions of dry toluene and two times with freshly distilled methanol.

To this solid was added 50 mL of dry methanol and a solution of 12.9 g of phosphotungstic acid in methanol. The suspension was stirred overnight at room temperature under dry nitrogen and the solid separated and washed five times with 100 mL portions of methanol. The solid was dried at 60° for one hour.

To 400 mg of this modified support in 10 mL of acetone was added a solution of 20 micromoles of Rh(P(C$_6$H$_5$)$_3$)$_3$Cl in 2 mL of acetone after purging the flask with nitrogen. The resulting slurry was stirred at room temperature under nitrogen for 2 hours and the liquid extracted from the reactor. The solid was washed with 10 mL portions of acetone until there was no color in the wash liquid. The catalyst was dried under vacuum at room temperature for two hours and then used for the hydrogenation of 1-hexene using the procedure described in Example V. After each use the colorless liquid was removed from the reactor and fresh solvent and reactant were added for an additional hydrogenation. This catalyst was re-used eight times with no loss of activity nor any loss of the metal complex.

EXAMPLE XVIII

This example illustrates the use of this technique for the supporting of a non-precious metal complex. The support used is a titanium alkoxide modified silica.

One gram of the titanium alkoxide modified silica support with the attached PTA as described in Example XVII and 10 mL of tetrahydrofuran (THF) were placed in a flask. After purging the flask with nitrogen, 65.4 mg of $NiCl_2(TPP)_2$ dissolved in 1 mL of THF was added and the resulting slurry was stirred at room temperature for 2 hours (TPP= triphenylphosphine). The liquid was extracted and the solid washed 5 times with 20 mL portions of dry THF. The catalyst was dried under vacuum at room temperature for two hours and used immediately.

To 500 mg of this catalyst was added 6 mL of THF and 1.62 mL of a cold solution containing 2.9 mmole of phenyl lithium. The mixture was cooled to 0° C. under stirring and 0.42 mL of $B(OCH_3)_3$ (3.62 mmol) was slowly added followed by 0.167 ml (1.44 mmole) of allyl methyl carbonate and the temperature was allowed to rise to ambient. The mixture was then heated, with stirring, at 60° C. for 12 hours. The liquid was separated from the solid catalyst and poured into a mixture of 20 mL of pentane and 20 mL of saturated ammonium chloride solution. After vigorous shaking the organic layer was separated and filtered through a Celite pad. After drying and evaporation of the organic phase, gas chromatographic analysis of the residue using an HP-1 column showed that 3-phenylpropene-1 was formed in a yield identical to that obtained using the soluble nickel catalyst.

While the invention has been particularly shown and described with respect to preferred embodiments thereof, it will be understood by those skilled in the art that the foregoing and other changes in form and detail may be made without departing from the spirit and scope of the invention.

TABLE 1[a]

| Support | Use # | Rate[b] | ee |
|---|---|---|---|
| Montmorillonite | 1 | 0.11 | 92% |
| K clay | 3 | 0.80 | 92% |
|  | 1[c] | 0.18 | 92% |
|  | 3[c] | 0.54 | 94% |
| Carbon | 1 | 0.07 | 75% |
|  | 3 | 0.50 | 78% |

[a]Examples of data obtained on hydrogenation of 2-acetamidoacrylic acid methyl ester over supported Rh(DIPAMP)/PTA catalysts supported on Montmorillonite clay and carbon prepared using the procedure described in Example I.
[b]moles $H_2$/mole Rh/min
[c]Data obtained using a catalyst which had been stored in air for about eight months.

TABLE 2[a]

| Support | Use # | Rate[a] | ee |
|---|---|---|---|
| Montmorillonite K | 1 | 0.18 | 76% |
|  | 3 | 0.56 | 91% |
| Carbon | 1 | 0.07 | 83% |
|  | 3 | 0.40 | 90% |
| Alumina | 1 | 0.32 | 90% |
|  | 3 | 1.67 | 92% |
| Lanthana | 1 | 0.38 | 91% |
|  | 3 | 0.44 | 92% |

[a]Examples of data obtained on hydrogenation of 2-acetamidoacrylic acid methyl ester over supported Rh(DIPAMP)/PTA catalysts supported on different supports prepared using the procedure described in Example III.
[b]moles $H_2$/mole Rh/min TABLE 3[a]

| Heteropoly Acid | Use # | Rate[b] | ee |
|---|---|---|---|
| Phosphotungstic | 1 | 0.18 | 76% |
|  | 3 | 0.56 | 91% |
| Silicotungstic | 1 | 0.04 | 55% |
|  | 3 | 0.31 | 87% |
| Silicomolybdic | 1 | 0.23 | 92% |
|  | 3 | 1.13 | 94% |

[a]Examples of data obtained on hydrogenation of 2-acetamidoacrylic acid methyl ester over supported Rh(DIPAMP)/heteropoly acid catalysts supported on Montmorillonite K clay with different heteropoly acids prepared using the procedure described in Example III.
[b]moles $H_2$/mole Rh/min TABLE 4[a]

|  |  | Supported[b] |  | Soluble[c] |  |
|---|---|---|---|---|---|
| Catalyst | Use # | Rate[d] | ee | Rate[d] | ee |
| Rh(DIPAMP) | 1 | 0.32 | 90% | 0.25 | 76% |
|  | 3 | 1.67 | 92% | na | na |
| Rh(PROPHOS) | 1 | 2.0 | 68% | 0.26 | 66% |
|  | 3 | 2.6 | 63% | na | na |
| Rh(Me-DUPHOS) | 1 | 1.8 | 83% | 3.3 | 96% |
|  | 3 | 4.4 | 95% | na | na |

[a]Examples of data obtained on hydrogenation of 2-acetamidoacrylic acid methyl ester over different rhodium complexes heteropoly acid catalysts supported on gamma alumina which had been treated with phosphotungstic acid using the procedure described in Example III.
[b]Alumina/PTA supported metal catalysts.
[c]Unsupported metal catalysts in solution.
[d]moles $H_2$/mole Rh/min TABLE 5[a]

|  |  | Isomerization | Hydroformylation |  |  |
|---|---|---|---|---|---|
| Catalyst | % Conv. | %1 | %2 | %3 | %4 | 2/3 |
| Soluble[b] | 90 | — | 48 | 38 | 9 | 1.3 |
| Supported[c] (1st use) | 78 | 15 | 49 | 29 | — | 1.7 |
| (2nd use) | 65 | 12 | 40 | 24 | — | 1.6 |
| (3rd use) | 70 | 10 | 44 | 25 | — | 1.8 |

[a]Examples of data obtained on hydroformylation of 1-heptene over a Rh(P $(C_6H_5)_3)_3$Cl/PTA/Montmorillonite clay catalyst prepared using the procedure described in Example III with the reaction run using the procedure described in Example XV. The compound identities are listed in Example XV
[b]Unsupported metal catalyst in solution.
[c]Montmorillonite/PTA supported metal catalyst.

TABLE 6[a]

| Catalyst | Rxn Time | Conv. | %5 | %6 | %7 | ee % | 5/6 | 5 + 6/7 |
|---|---|---|---|---|---|---|---|---|
| Soluble[b] | 24 hr | 96% | 56 | 6 | 38 | 26 | 9.3 | 1.6 |
| Supported[c] (First Use) | 12 hr | 100% | 76 | 1.5 | 22 | 27 | 50 | 3.5 |
| Second Use | 12 hr | 100% | 78 | 1.2 | 21 | 31 | 65 | 3.8 |
| Fourth Use | 12 hr | 100% | 78 | 1 | 21 | 30 | 78 | 3.9 |

[a]Examples of data obtained on allylation of sodium dimethylmalonate by 2-butenyl acetate over a Pd(R,R-BINAP)/PTA/Carbon catalyst prepared using the procedure described in Example IV with the reaction run using the procedure described in Example XVI. The compound identities are listed in Example XVI
[b]Unsupported metal catalyst in solution.
[c]Carbon/PTA supported metal catalyst.

What is claimed is:

1. A process for the hydrogenation of a substituted α,β unsaturated acid or ester, said process comprising contacting a substituted α,β unsaturated acid or ester of the formula:

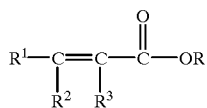

wherein $R^1$, $R^2$ and $R^3$ are the same or different and are hydrogen, alkyl containing from 1 to about 35 carbon atoms, alkenyl containing from 1 to about 35 carbon atoms, alkynyl containing from 1 to about 35 carbon atoms, aryl containing about 6 to about 18 carbon atoms, amine, amide, or alkoxide containing from 1 to about 35 carbons atoms; and R is hydrogen or alkyl containing from 1 to about 35 carbon atoms with a supported catalyst comprising a support, an anchoring agent, and a metal complex, wherein said anchoring agent is a heteropoly acid, its lacunar or other crystalline or non-crystalline phase or the respective anion and wherein said anchoring agent forms a bridge between the support and the metal complex by direct interaction with the metal of said metal complex in $H_2$ under conditions effective to selectively hydrogenate the substituted α,β unsaturated acid or ester into a desired product.

2. The process of claim 1 wherein said substituted α,β unsaturated acid or ester is 2-acetamidocinnamic acid methyl ester, 2-acetamidocinnamic acid, 2-acetamido acrylic acid methyl ester, 2-acetamido acrylic acid, dimethylitaconate, itaconic acid, 2-methylpentenoic acid, 2-methylhexenoic acid or 2-(6-methoxy-2-naphthyl)acrylic acid.

3. The process of claim 2 wherein said substituted α,β unsaturated acid or ester is a prochiral substituted α,β unsaturated acid or ester and said catalyst is a chiral catalyst.

4. The process of claim 2 wherein said hydrogenation occurs in the vapor or liquid phase.

5. The process of claim 2 wherein said hydrogenation is run in a batch mode or in a continuous process.

6. A process for the hydroformylation of alkenes into their corresponding aldehydes or alcohols, said process comprising contacting an alkene containing from 2 to about 35 carbon atoms with a supported catalyst comprising a support, an anchoring agent, and a metal complex, wherein said anchoring agent is a heteropoly acid, its lacunar or other crystalline or non-crystalline phase or the respective anion and wherein said anchoring agent forms a bridge between the support and the metal complex by direct interaction with the metal of said metal complex in the presence of $H_2$ and CO under conditions effective to convert said alkene to a corresponding aldehyde and/or acid.

7. The process of claim 1 wherein said support is selected from the group consisting of metal oxides, carbon, resins and polymers.

8. The process of claim 7 wherein the metal oxide is selected from the group consisting of alumina, silica, titania, lanthana, zeolites and clays.

9. The process of claim 7 wherein the support is a treated support.

10. The process of claim 9 wherein said treated support material is obtained by calcining said support or contacting said support with a modifier.

11. The process of claim 10 wherein the modifier is a metal alkoxide.

12. The process of claim 11 wherein said metal alkoxide is titanium alkoxide, aluminum alkoxide, silane alkoxide or vanadium alkoxide.

13. The process of claim 1 wherein said heteropoly acid is a Keggin type, Dawson type, Waugh type, Anderson type or Silverton type and said anion is an anion of the heteropoly acid.

14. The process of claim 13 wherein the Keggin type of said heteropoly acid is phosphotungstic acid, phosphomolybdic acid or silicotungstic acid or the anions thereof.

15. The process of claim 1 wherein the metal complex is a catalytically active material which contains at least one metal atom or ion from Group IIIB, IVB, VB, VIB, VIIB, VIII, IB or IIB of the Periodic Table of Elements to which one or more ligands are attached.

16. The process of claim 15 wherein said metal atom or ion is from Group VIII of the Periodic Table of Elements.

17. The process of claim 15 wherein said ligand is selected from the group consisting of phosphines, amines, carbonyl, alkenes, dienes, halides, (R,R) or (S,S)2,2'-bis(diphenylphosphino)-1,1'-binapthyl(BINAP), (2S,3S)-bis(diphenylphosphino)butane (CHIRAPHOS), cyclooctadiene (COD), (R,R)-1,2-bis[(2 methoxyphenyl)phenylphosphine]ethane (DIPAMP), 1,2-bis(2R,5R)-2,5 (dimethylphospholano)benzene (Me-DUPHOS) (R)1,2-bis(diphenylphosphino)propane (PROPHOS), 2,3-O-isopropylidene-2,3-dihydroxy-1,4-bis(diphenylphosphino)butane (DIOP) and mixtures thereof.

18. The process of claim 6 wherein said support is selected from the group consisting of metal oxides, carbon, resins and polymers.

19. The process of claim 18 wherein the metal oxide is selected from the group consisting of alumina, silica, titania, lanthana, zeolites and clays.

20. The process of claim 6 wherein the support is a treated support.

21. The process of claim 20 wherein said treated support material is obtained by calcining said support or contacting said support with a modifier.

22. The process of claim 21 wherein the modifier is a metal alkoxide.

23. The process of claim 22 wherein said metal alkoxide is titanium alkoxide, aluminum alkoxide, silane alkoxide or vanadium alkoxide.

24. The process of claim 6 wherein said heteropoly acid is a Keggin type, Dawson type, Waugh type, Anderson type or Silverton type and said anion is an anion of the heteropoly acid.

25. The process of claim 24 wherein the Keggin type of said heteropoly acid is phosphotungstic acid, phosphomolybdic acid or silicotungstic acid or the anions thereof.

26. The process of claim 6 wherein the metal complex is a catalytically active material which contains at least one metal atom or ion from Group IIIB, IVB, VB, VIB, VIIB, VIII, IB or IIB of the Periodic Table of Elements to which one or more ligands are attached.

27. The process of claim 26 wherein said metal atom or ion is from Group VIII of the Periodic Table of Elements.

28. The process of claim 26 wherein said ligand is selected from the group consisting of phosphines, amines, carbonyl, alkenes, dienes, halides, (R,R) or (S,S)2,2'-bis(diphenylphosphino)-1,1'-binapthyl(BINAP), (2S,3S)-bis(diphenylphosphino)butane (CHIRAPHOS), cyclooctadiene (COD), (R,R)-1,2-bis[(2 methoxyphenyl)phenylphosphine]ethane (DIPAMP), 1,2-bis(2R,5R)-2,5 (dimethylphopholano)benzene (Me-DUPHOS (R)1,2-bis(diphenylphosphino)propane (PROPHOS), 2,3-O-isopropylidene-2,3-dihydroxy-1,4-bis(diphenylphosphino)butane (DIOP) and mixtures thereof.

29. A process for forming a C—X bond, wherein C is carbon and X is H, C, O, halogen, Si, alkoxy, or N comprising contacting an organic compound requiring formation of said C—X bond with a support catalyst in the presence of a reactant under conditions capable of forming said C—X bond in said organic compound, wherein said supported catalyst comprises a support, an anchoring agent, and a metal complex, said anchoring agent is a heteropoly acid, its lacunar or other crystalline or non-crystalline or the respective anion, and said anchoring agent forms a bridge between the support and the metal complex by direct interaction with the metal of said metal complex.

* * * * *

UNITED STATES PATENT AND TRADEMARK OFFICE
CERTIFICATE OF CORRECTION

PATENT NO. : 6,005,148
DATED : December 21, 1999
INVENTOR(S) : Setrak K. Tanielyan It is certified that error appears in the above-identified patent and that said Letters Patent is hereby corrected as shown below:

Title page,
Item [56], References Cited, OTHER PUBLICATIONS, "phtalate" should read -- phthalate --

Column 20,
Line 62, "dimethylphopholano" should read -- dimethylphospholano --

Signed and Sealed this

Thirtieth Day of April, 2002

Attest:

JAMES E. ROGAN
Attesting Officer    Director of the United States Patent and Trademark Office